United States Patent [19]

Zimmerman et al.

[11] Patent Number: 5,116,667
[45] Date of Patent: * May 26, 1992

[54] COMPOSTIBLE COMPOSITIONS AND PRODUCTS

[75] Inventors: Robert R. Zimmerman, Pickerington; Tamela A. Viers, Columbus, both of Ohio

[73] Assignee: Century Adhesives Inc., Columbus, Ohio

[ * ] Notice: The portion of the term of this patent subsequent to Aug. 6, 2008 has been disclaimed.

[21] Appl. No.: 564,061

[22] Filed: Aug. 8, 1990

[51] Int. Cl.$^5$ ............................................. B32B 25/12
[52] U.S. Cl. .................. 428/220; 428/478.2; 428/484; 428/492
[58] Field of Search ............ 428/492, 486, 220, 478.2, 428/484; 604/364, 373, 372, 358

[56] References Cited

U.S. PATENT DOCUMENTS

| | | | |
|---|---|---|---|
| 1,564,498 | 12/1925 | Thomas | 604/364 |
| 1,979,899 | 11/1934 | O'Brien et al. | 604/364 X |
| 3,563,244 | 2/1971 | Asaka | 604/364 |
| 3,616,797 | 11/1971 | Champaigne, Jr. et al. | 604/372 |
| 3,654,064 | 4/1972 | Laumann | 428/486 |
| 3,838,692 | 10/1974 | Levesque | 604/372 X |
| 5,037,410 | 8/1991 | Zimmerman et al. | 604/358 |

Primary Examiner—Thomas J. Herbert, Jr.
Attorney, Agent, or Firm—Carroll F. Palmer

[57] ABSTRACT

Compostible compositions in the form of homogeneous mixtures containing 20-80% by weight unvulcanized, uncured C4-C6 alkadiene elastomer, e.g., natural rubber, 5-20% of modifier, e.g., casein, dextrose, starch or mixtures thereof, 1-40% filler, e.g., titanium dioxide or fibrous clay, 0-30% wax, e.g., carnauba wax, 0-40% styrene resin, e.g., polystyrene, 0-10% additive, e.g., bis-steramide, and 0-20% yeast are disclosed. Preferably such compositions are prepared as aqueous dispersions that can be converted by conventional casting procedures into thin sheets, e.g., about 1 to 10 mils, having useful tensile strength, elongation, flexibility and moisture barrier properties.

12 Claims, No Drawings

COMPOSTIBLE COMPOSITIONS AND PRODUCTS

BACKGROUND OF THE INVENTION

1. Field of the Invention

This application relates to compostible compositions and products. More particularly, it concerns unique compostible compositions comprising elastomers and sheets and like products made thereof.

2. Description of the Prior Art

The disposal of solid waste has become a worldwide problem because of its magnitude with great economic and environmental ramifications. As a consequence, producers of disposable products, e.g., diapers, containers, etc., are under increasing pressure to assist in providing a solution, particularly in providing products that will be environmentally acceptable in solid waste landfills. Several approaches have been taken to address this concern. One has been to employ product construction materials that can be degraded by microorganisms or enzymes or other substances that they secret. This is particularly important if the disposalable product will find its way into a compost facility.

There has been a concerted effort to educate the general public concerning the solid waste disposal problems and to get its cooperation in helping to mitigate the problems, e.g., to participate in dividing trash into classes or recyclable items. This has resulted in the use of the term biodegradable to indicate that a material so classified is environmentally acceptable for disposal in solid waste landfills. However, this term appears to be too ambiguous for use by disposable article industries and government agencies so a more specific term has evolved, namely, compostible, which signifies that a material so classified is capable of controlled biological decomposition under predominantly aerobic conditions into material which can be easily and safely stored, handled and used without creating a threat to public health and/or the environment.

Although the environmental aspects of waste disposal have received great attention in recent years, waste disposal problems have concerned disposalable product manufactures for many years resulting in many disclosures for product improvements seeking to assist in mitigation of the problems. For example, see U.S. Pat. Nos. 1,564,498; 1,979,899; 3,563,244; 3,616,797; 3,654,064 and 3,838,692.

The present invention further addresses the environmental aspects of solid waste disposal of throw-away products and provides unique compositions and products to assist in mitigation thereof.

OBJECTS

A principal object of the invention is the provision of new compostible compositions and products.

Another object is the provision of unique compostible compositions comprising elastomers that may be formed into flexible sheets having substantial strength properties and which are compostible.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

SUMMARY OF THE INVENTION

The objects are accomplished in part in accordance with the invention by the provision of compostible compositions comprising a homogeneous mixture of 50 to 80% unvulcanized, uncured C4-C6 alkadiene elastomer, 5 to 20% of casein or equivalent animal and plant protein, dextrose, starch or mixtures thereof, 1 to 40% of filler, 0 to 30% wax, 0 to 40% styrene polymer, 0–10% additive and 0 to 20% yeast.

In some preferred embodiments, the elastomer is natural rubber, the inorganic filler is selected from titanium dioxide and clay and the styrene polymer is selected from polystyrene and styrene/alkadiene copolymers. By way of example, a preferred compostible composition of the invention comprises an unvulcanized, uncured homogeneous mixture of a major percentage of natural rubber with lesser percentages of casein and inorganic filler in such proportions that a cast sheet of the composition with a thickness of 1 to 2 mils has a tensile strength of at least 200 grams per inch of width and 400 grams per inch of width at an elongation of at least 400%. Such a composition can, for example consist essentially of 35–75% unvulcanized, uncured natural rubber, 10–15% casein, 10–20% wax and 5–20% inorganic filler.

Preferred compositions of the invention are aqueous dispersions of the essential ingredients, e.g., emulsions or other aqueous dispersions containing between about 10 to 90% solids and, particularly 25% to 80% solids. In this regard and throughout this specification and claims, all parts are by weight and all percentages of the material in question are by weight based on the total weight of the composition containing same.

The objects are further accomplished by the provision of flexible, compostible sheets about 1 to 10 mils thick composed of acomprising a homogeneous mixture of 50 to 80% unvulcanized, uncured C4–C6 alkadiene elastomer, 5 to 20% of casein or equivalent animal and plant protein, dextrose, starch or mixtures thereof, 1 to 40% of filler, 0 to 30% wax, 0 to 40% styrene polymer, 0–10% additive and 0 to 20% yeast.

Flexible, compostible sheets about 1 to 10 mils thick can be prepared by casting a layer of the dispersion of compositions of the invention onto a surface and then evaporating all volatile liquid form the cast layer, particularly at an elevated temperature, e.g., 100°–200° C. The sheets may also be prepared by extrusion of the new compostible compositions.

Typically cast sheets of the invention with a thickness of 1 to 2 mils have a tensile strength of at least 100 grams per inch of width at 100% elongation and an ultimate tensile strength of at least 400 grams per inch of width at an elongation of at least 400%.

DESCRIPTION OF THE PREFERRED EMBODIMENTS

A more complete understanding of the invention can be obtained by reference to preferred embodiments of the invention which are illustrated by the following specific examples of the production of unique sheets used in construction of new articles of the invention. It will be apparent to those skilled in the art that the examples involve use of materials and reagents that are commercially available from known sources, e.g., chemical supply houses, so no details are given respecting them, although manufacturing sources may be indicated for assistance in replicating the compositions and products.

In the examples, the percentages stated in [brackets] after each ingredient indicate the percentage by weight of the solids content of the composition created in the example. Further, all parts are by weight.

EXAMPLE 1

A blender is charged with 41.4 parts of natural rubber [67%] latex (62% solids), 31.8 parts of casein [12.5%] aqueous dispersion (15% solids) and 19.1 parts of carnauba wax [16.5%] slurry (33% solids). With the blender operating a slow speed, 1.3 parts of titanium dioxide [3.4%] slurried in 6.4 parts of water is slowly added to the mixture which is then mixed for 20 minutes to produce a homogeneous aqueous dispersion.

EXAMPLE 2

A thin layer of the dispersion of Example 1 was cast on release coated paper using a #20 drawdown bar and dried at about 120° C. for about 1 hour. The resulting sheet of about 1-1.25 mil thickness had at an elongation of 450-500% an ultimate tensile strength of 400-500 grams per inch of width and required a force of 275 grams to produce a 100% elongation when tested in accordance the ASTM standard test methods D-882-83 for tensile properties of thin plastic sheeting.

The sheet is also tested for water permeability by stretching a section of it across a pair of supports and then placing the tip of a pipette containing a column of water six inches high against the top surface of the suspended sheet. After 30 minutes, no water has appeared on the bottom surface of the sheet under the pipette tip.

EXAMPLE 3

The procedure of Example 1 is repeated except that a 10% aqueous dispersion of 4 parts of yeast [9.5%] is charged into the blender with the rubber [61.0%], casein [11.3%], wax [15.0%] and $TiO_2$ [3.0%]. A cast sheet formed and tested as in Example 2 exhibited, after 5 days storage at ambient temperature, an ultimate tensile strength of 220-270 grams/in.width at an elongation of 600-700% and required a pull of 130-140 grams to produce an elongation of 100%.

EXAMPLE 4

A blender is charged with 39.9 parts of natural rubber [61.3%] latex (62% solids), 30.7 parts of casein [11.4%] aqueous dispersion (15% solids) and 18.4 parts of carnauba wax [15.0%] slurry (33% solids). With the blender operating a slow speed, 1.2 parts of titanium dioxide [3.0%] slurried in 6.4 parts of water and 9.8 part of polystyrene [9.2%] emulsion (37.8% solids) are slowly added to the mixture which is then mixed for 20 minutes to produce a homogeneous aqueous dispersion.

EXAMPLE 5

Using the procedure of Example 2, a sheet of about 1 mil thickness is cast from the aqueous dispersion of Example 4. Under test pursuant to ASTM 882-83, the sheet at an breaking elongation of 450-500% had a tensile strength of 750-950 grams and required a pull of 300-320 grams for a 100% elongation.

EXAMPLE 6

A specimen of the sheet prepared in Example 2 is placed in a compost bin on which a small amount of yeast dispersion had been sprayed and mixed with the compost. After three weeks of burial in the compost pile, it is found that the sheet is completely decomposed. Hence, no tensile tests are performed.

EXAMPLE 7

A blender is charged with 7.9 parts of dry clay (Nytal 400 TM )[21.7%], 2.0 parts of titanium dioxide [4.3%] aqueous slurry (77% solids), and 13.8 parts water containing 0.1% surface active agent (Surfynol 440 TM ). With the blender operating at slow speed, 15.8 parts of natural rubber [27.0%] latex (62% solids), 19.8 parts of carnauba wax [18.0%] slurry (33% solids), 24.9 parts of casein [10.2%] solution (15% solids) and 15.8 parts of resin modified styrene-isoprene-styrene copolymer [18.7] emulsion (43% solids) (Prinlin B7137X-1 TM ) were added and mixing is continued for 30 minutes to produce an cream-like aqueous dispersion.

Thin cast sheets formed as described in Example 2 exhibit properties comparable to those of Examples 2 and 5.

EXAMPLE 8

The procedures of Examples 1, 4 and 7 are repeated but with substitution of dextrose, starch or mixtures thereof for some or all of the casein. When cast sheets with thickness of about 1 to 2 mils of the resulting compositions are prepared and tested as in Example 2, they are all found to have a tensile strength of at least 200 grams per inch of width and to be water impermeable for at least 30 minutes against a six inch head of water.

While natural rubber is a preferred elastomer for use in forming the moisture barrier sheets used in construction of articles of the invention, other C4–C6 alkadiene elastomers, including mixtures thereof, may be used. Examples include styrene-butadiene rubbers, acrylonitrile-butadiene rubbers, butadiene rubbers, acrylate-butadiene rubbers, and elastomeric styrene-butadiene, styrene-isoprene, styrene-isoprene-butadiene block copolymers and equivalent elastomers Casein is a preferred modifier for use in production of compostible sheets of the invention. However, this may be substituted, in whole or in part, by equivalent animal and plant proteins, e.g., soybean protein, dextrose, starch and mixtures thereof.

A variety of fillers may be used in formulation of the new compostible sheets, e.g., caulk, garnet, clays, fume silica, talc, lampblack, graphite, kaolin, magnesite, mica, quartz alumina, aluminum stearate, magnesia, barium sulfate, chrome oxide, cellulose fibers, nylon monofilament cuttings, and equivalent materials. Inorganic fillers are preferred.

A variety of natural and synthetic waxes, including mixtures thereof, may be used in production of the new compostible sheets, e.g., paraffin wax, beeswax, spermaceti, and equivalent materials, including hydrogenated fats or the like.

Styrene resins useable in accordance with the invention are those styrene homopolymers or copolymers that are resinous in nature rather than elastomeric, including polystyrene, resinous styrene-butadiene, styrene-isoprene, styrene-isoprene-butadiene block copolymers, styrene-alkyl acrylate copolymers, styrene-vinyl carboxylate copolymers and equivalent styrene resins.

In addition to the various components elucidated above, the compostible sheets of the invention may contain minor amounts, e.g., 0.1-10%, of various additives known in the art as useable in production of rubber-like sheets, e.g., processing aids such as bis-steramide and euricamide which improve slip. While additives can include anti-oxidants, stabilizers or the like, inclusion of such materials may be counterproductive in decreasing or destroying the compostibility of the new barrier sheets and articles. In this connection, inclusion of vulcanizers, curing agents and the like or bactericides or the like is to be avoided.

The embodiments of the invention in which an exclusion property or privilege is claimed are defined as follows:

1. A flexible, compostible sheet about 1 to 10 mils thick composed of a homogeneous mixture of the following ingredients in the stated percentages by weight:

| | |
|---|---|
| unvulcanized, uncured C4–C6 alkadiene elastomer | 20–80%, |
| modifier selected from animal and plant protein, dextrose, starch or mixtures thereof | 5–20%, |
| filler | 1–40%, |
| wax | 0–30%, |
| styrene resin | 0–40%, |
| additive | 0–10% |
| yeast | 0–20%. |

2. The sheet of claim 1 wherein said elastomer is natural rubber, said inorganic filler is selected from titanium dioxide and clay and said styrene resin is selected form polystyrene and resinous styrene/alkadiene copolymers.

3. A sheet of claim 1 having a thickness of 1 to 2 mils and a tensile strength of at least 100 grams per inch of width.

4. The sheet of claim 1 consisting essentially of the following ingredients in the stated percentages by weight:

| | |
|---|---|
| unvulcanized, uncured natural rubber | 65–75%, |
| casein | 10–15%, |
| wax | 10–20%, |
| filler | 5–20%. |

5. A compostible composition comprising an unvulcanized, uncured homogeneous mixture of a major percentage of natural rubber with lesser percentages of casein and inorganic filler, wherein a cast of sheet of said composition having a thickness of 1 to 2 mils has a tensile strength of at least 200 grams per inch of width.

6. A compostible composition comprising an homogeneous mixture of the following ingredients in the stated percentages by weight:

| | |
|---|---|
| unvulcanized, uncured C4–C6 alkadiene elastomer | 20–80%. |
| modifier selected from animal and plant protein, dextrose, starch or mixtures thereof | 5–20%. |
| filler | 1–40%, |
| wax | 0–30%. |
| styrene resin | 0–40%. |
| additive | 0–10% |
| yeast | 0–20%. |

7. The composition of claim 6 wherein said elastomer is natural rubber, said filler is selected from titanium dioxide and clay and said styrene resin is selected from polystyrene and resinous styrene/alkadiene copolymers.

8. A composition of claim 6 wherein a cast sheet thereof having a thickness of 1 to 2 mils has a tensile strength of at least 100 grams per inch of width.

9. The composition of claim 6 consisting essentially of the following ingredients in the stated percentages by weight:

| | |
|---|---|
| unvulcanized, uncured natural rubber | 65–75%, |
| casein | 10–15%, |
| wax | 10–20%. |
| inorganic filler | 5–20%. |

10. A composition of claim 9 wherein a cast sheet thereof having a thickness of 1 to 2 mils has a tensile strength of at least 400 grams per inch of width at an elongation of at least 400%.

11. The composition of claim 6 which is a aqueous dispersion of said ingredients.

12. A flexible, compostible non-fibrous sheet about 1 to 10 mils thick prepared by casting a layer of said dispersion of claim 11 onto a surface and evaporating volatiles from said cast layer at an elevated temperature.

* * * * *